United States Patent [19]
Yao et al.

[11] Patent Number: 5,728,952
[45] Date of Patent: Mar. 17, 1998

[54] VIBRATION MEASURING INSTRUMENT

[75] Inventors: Hironobu Yao; Hiroyuki Yoshimura; Masato Takahashi; Michihiko Tsuruoka; Iwao Matsumoto; Masakazu Kawakami; Keita Okawa, all of Kawasaki, Japan

[73] Assignee: Fuji Electric Co., Ltd., Kanagawa, Japan

[21] Appl. No.: 525,466

[22] Filed: Sep. 8, 1995

[30] Foreign Application Priority Data

Sep. 9, 1994 [JP] Japan ................. 6-215663
Feb. 6, 1995 [JP] Japan ................. 7-017588

[51] Int. Cl.⁶ ................................................. G01F 1/84
[52] U.S. Cl. ................................ 73/861.357; 73/32 A
[58] Field of Search .................... 73/861.355, 861.356, 73/861.357, 861.351, 32 A

[56] References Cited

U.S. PATENT DOCUMENTS

| | | | |
|---|---|---|---|
| 5,054,326 | 10/1991 | Mattar | 73/861.38 |
| 5,115,683 | 5/1992 | Pratt | 73/861.355 |
| 5,373,745 | 12/1994 | Cage | 73/861.356 |
| 5,398,554 | 3/1995 | Ogawa et al. | 73/861.357 |
| 5,448,921 | 9/1995 | Cage et al. | 73/861.357 |
| 5,469,748 | 11/1995 | Kalotay | 73/861.38 |

FOREIGN PATENT DOCUMENTS

| | | | |
|---|---|---|---|
| 0698783 | 2/1996 | European Pat. Off. | G01F 1/84 |
| 2635866 | 3/1990 | France | G01F 1/84 |
| 3923409 | 1/1991 | Germany | G01F 1/84 |
| 4224379 | 12/1993 | Germany | G01D 3/04 |
| 19525253 | 1/1996 | Germany | G01F 1/84 |
| 19634663 | 8/1996 | Germany . | |
| 5-69425 | 5/1993 | Japan | G01F 1/84 |
| 6-63958 | 6/1994 | Japan | G01N 9/00 |
| 6-94501 | 6/1994 | Japan | G01F 1/84 |
| 8706691 | 11/1987 | WIPO | G01F 1/84 |
| 8802477 | 4/1988 | WIPO | G01F 1/84 |
| 8802853 | 4/1988 | WIPO | G01N 9/00 |
| 8900679 | 1/1989 | WIPO | G01F 1/84 |

*Primary Examiner*—Richard Chilcot
*Assistant Examiner*—Harshad Patel
*Attorney, Agent, or Firm*—Elman & Associates

[57] ABSTRACT

The precision of phase difference obtained by a phase difference calculating unit is improved by correction through outputs of a frequency ratio calculating unit and a temperature calculating unit considering that the phase or time difference of each output signal of a vibration sensor indicating the mass flow or density of a fluid is a function of the temperature and axial force on a measurement pipe, or that the axial force is a function of the ratio between two resonant frequencies.

13 Claims, 9 Drawing Sheets

VIBRATION MEASURING INSTRUMENT

BACKGROUND OF THE INVENTION

1. Field of the Invention

The present invention relates to a mass flowmeter for fluid, comprising at least one measurement pipe for measuring a mass flow based on the Coriolis force generated by the mass flow of the fluid flowing through the measurement pipe, to a vibration density meter for measuring the density of the fluid depending on the variation of the resonant frequency of the measurement pipe which alters with the density of the fluid in the above described measurement pipe, and to a vibration measuring instrument having the functions of both of the above described meters, and especially to the vibration measuring instrument and vibration measuring instrument adjusting device capable of adjusting a measured value depending on the fluid temperature, atmospheric temperature, and axial force (stress).

2. Description of the Prior Art

Figure 1:
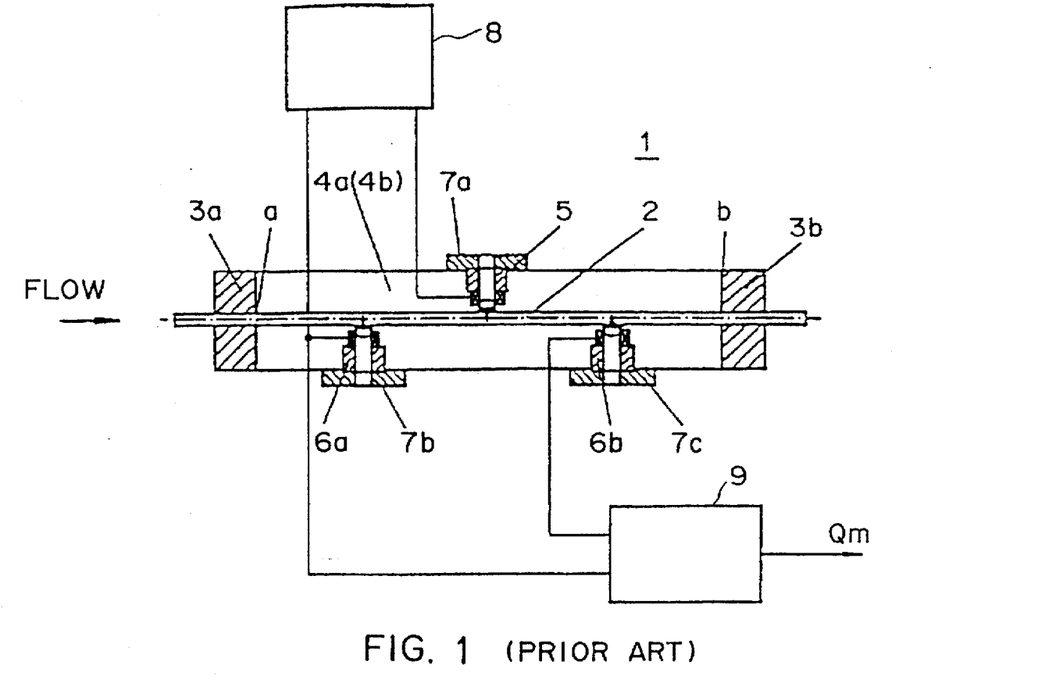
FIG. 1 shows the configuration of the conventional vibration measuring instrument.

FIG. 1 shows the configuration of the conventional straight-pipe mass flowmeter.

A detecting unit 1 comprises a straight measurement pipe 2; right and left fixtures 3a and 3b for fixing the vibrating sections a and b of the measurement pipe 2; supporters 4a and 4b (only 4a is shown in FIG. 1) fixed to the fixtures 3a and 3b with screws or by soldering, etc., or designed as being combined with the fixtures 3a and 3b so that the vibrations of the fixtures 3a and 3b cancel each other; and a vibration generator 5, comprising coils fixed to the supporters 4a and 4b with an adapter 7a and a magnet fixed at the central portion of the measurement pipe 2, for vibrating of the measurement pipe 2 at its resonant frequency.

The detecting unit 1 further comprises, similar to the vibration generator 5, speed detecting sensors (or displacement sensors or acceleration sensors) 6a and 6b, comprising magnets fixed symmetrically to the vibration generator 5 on the measurement pipe 2, with the coils fixed to the supporters 4a and 4b with the adapters 7b and 7c, for detecting the vibration of the measurement pipe 2; a drive circuit 8 for receiving an output from the speed detecting sensor 6a and outputting a drive signal to the vibration generator 5 so that the signal amplitude can be kept constant; and a signal processing circuit 9 for outputting a mass flow signal Qm based on the phase difference (time difference) of the signal from the speed detecting sensors 6a and 6b.

Assume that the flow of the fluid is zero in the detecting unit 1, designed as described above.

That is, the measurement pipe 2 is vibrated at the resonant frequency of the vibration generator 5 and drive circuit 8. Since the speed detecting sensors 6a and 6b are mounted symmetrically about the center of the measurement pipe 2, signals of equal amplitude can be obtained without phase difference from the speed detecting sensors 6a and 6b.

Figure 2:
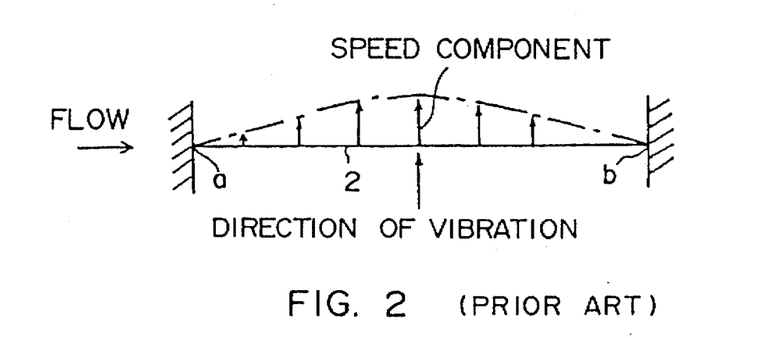
FIG. 2 is a graph of the acceleration working on the fluid.
Figure 3:
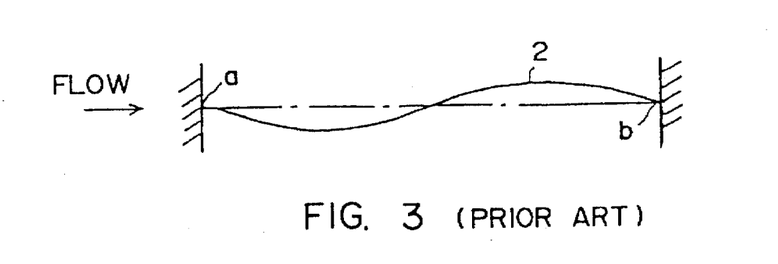
FIG. 3 is a graph of the influence of the axial force of the fluid working on a measurement pipe.

If the fluid flows through the vibrating measurement pipe 2, the speed component in the vibration direction is increased as shown in FIG. 2, as the fluid flows from the section a of the measurement pipe 2 toward the center of the measurement pipe 2. Therefore, the fluid flowing through the measurement pipe 2 receives positive acceleration from the measurement pipe 2 in the vibration direction. As a result, the reaction of the fluid is passed to the measurement pipe 2, and the phase of the vibration is delayed at the section a of the measurement pipe 2 toward the center of the measurement pipe 2, as shown in FIG. 3. Since the speed component in the vibration direction is decreased as the fluid flows from the center of the measurement pipe 2 to the section b, the fluid flowing through the measurement pipe 2 receives negative acceleration from the measurement pipe 2 in the vibration direction. As a result, the reaction of the fluid is passed to the measurement pipe 2, and the phase of the vibration is advanced at the center of the measurement pipe 2 toward the section b of the measurement pipe 2 as shown in FIG. 3.

The variation in the measurement pipe 2 is described by referring to the following equations.

The displacement of the displacement sensor 6a is represented by the following equation, according to the displacement of the horizontal vibration of the measurement pipe 2 through resonance.

$$Ya = \eta(a) \sin \omega_n t \qquad (1)$$

where $\eta(a)$: function indicating the amplitude of the position a in the axial direction of the measurement pipe 2

$\omega_n$: resonant frequency of the measurement pipe 2.

The deformation of the measurement pipe 2 by the reaction of the fluid in the displacement sensor 6a is represented by the following equation (2).

$$ya = -2L^3 Qm\omega_n \eta c (a) \cos \omega_n t/EI \qquad (2)$$

where

L: length of the measurement pipe 2

E: Young's modulus for the measurement pipe 2

I: Sectional secondary moment of the measurement pipe 2

Qm: mass flow of fluid in the measurement pipe 2 qc (a): deformation amplitude function of the measurement pipe 2 according to the reaction from the fluid at the position a in the axial direction of the measurement pipe 2.

The actual deformation of the measurement pipe 2 is determined by superimposing the deformation of the measurement pipe 2 as calculated by equation (2) onto the deformation of the measurement pipe 2 caused through the resonance calculated by equation (1). That is, the entire deformation of the measurement pipe 2 is calculated by combining equations (1) and (2) into equation (3).

$$\xi a = Ya + ya = A \sin(\omega_n t - \alpha) \qquad (3)$$

where $$A = [\eta(a)^2 + \{2L^3 Qm\omega_n \eta c (a)/EI\}^2]^{1/2} \qquad (4)$$

$$\alpha = 2L^3 Qm\omega_n \eta c (a)/EI\eta(a) \qquad (5)$$

Since the displacement sensors 6a and 6b are mounted symmetrically about the center of the measurement pipe 2, the displacement of the horizontal vibration of the measurement pipe 2 in the displacement sensor 6b is equal to the displacement of the displacement sensor 6a. That is;

$$Yb = Ya = \eta(a) \sin \omega_n t \qquad (6)$$

Since the reaction of the fluid in the displacement sensor 6b to the measurement pipe 2 is equal to that of the fluid in the displacement sensor 6a in the opposite direction, the following equation is defined.

$$yb = -ya = 2L^3 Qm\omega_n \eta c (a) \cos \omega_n t/EI \qquad (7)$$

Therefore, the deformation of the measurement pipe 2 is calculated by the following equation.

$$\xi b = Y_a - y_a = A \sin(\omega_n t + \alpha) \quad (8)$$

According to equations (3) and (8) above, the phase difference of $2\alpha$ is detected between the signals of the displacement sensors 6a and 6b. Equation (5) indicates that the phase difference of $2\alpha$ is proportional to the mass flow Qm. Therefore, the time difference between the signals of the displacement sensors 6a and 6b is calculated by the following equation (9).

$$\Delta t = 2\alpha/\omega_n = 2L^3 Qm\eta c \, (a)/EI\eta(a) \quad (9)$$

The resonant frequency of the measurement pipe 2 is calculated by the following equation (10).

$$\omega_n = \lambda^2/L^2 \cdot (EI/\rho)^{1/2} \quad (10)$$

where

λ: constant depending on the boundary conditions and vibration mode of the measurement pipe 2

ρ: line density including the measurement pipe 2 and the fluid in the measurement pipe 2.

If the temperature of the measurement pipe 2 changes, the phase and time differences between sensor output signals also change because of the temperature-dependency of Young's modulus E according to equations (5) or (9), even if the mass flow Qm is constant. Similarly, even though no density change is detected in the fluid to be measured, the resonant frequency $\omega_n$ in equation (10) changes.

In the above description, the axial force (stress) working on the measurement pipe 2 has not been considered. However, considering the influence of the axial force, the constant η indicating the amplitude of the measurement pipe 2 refers not only to the position of the measurement pipe 2 but also to the function of the axial force T. Therefore, the above described equation (1) can be represented as follows.

$$Y_a = \eta(a, T) \sin \omega_n t \quad (11)$$

Therefore, the above listed equations (5) and (9) can be represented as the following equations (12) and (13).

$$\alpha = 2L^3 Qm\omega_n \, \eta c \, (a, T)/EI\eta(a, T) \quad (12)$$

$$\Delta t = 2\alpha/\omega_n = 2L^3 Qm\eta c \, (a, T)/EI\eta(a, T) \quad (13)$$

That is, the phase and time differences generated in proportion to the mass flow depend on the axial force working on the measurement pipe 2. At this time, the resonant frequency $\omega_n$ of the measurement pipe 2 can be calculated by the following equation (14).

$$\omega_n = \lambda_n \, (T)^2/L^2 \cdot (EI/\rho)^{1/2} \quad (14)$$

The resonant frequency $\omega_n$ of the measurement pipe 2 also refers to a function of the axial force working on the measurement pipe 2.

Normally, the mass flowmeter measures the mass flow based on the Coriolis force generated by the mass flow of the fluid through the vibrating measurement pipe 2. If the temperature of the measurement pipe 2 changes with a variation in the temperature of the object fluid or the atmospheric temperature, the rigidity of the measurement pipe 2 changes with the temperature-dependency of Young's modulus for the measurement pipe 2, thereby changing the sensitivity to the Coriolis force and the measured flow value. If a Coriolis-type mass flowmeter having a straight measurement pipe is used, the axial force working on the measurement pipe changes with the expansion or contraction of the measurement pipe 2 and supporters 4a and 4b, because of the above described change in temperature. A change in the axial force also changes the sensitivity of the mass flow measurement.

Similarly, with the vibrating density meter, if the temperature of the measurement pipe 2 changes with a variation of the temperature of the object fluid or the atmospheric temperature, the resonant frequency changes with the temperature-dependency of Young's modulus for the measurement pipe 2, thereby generating erroneous measurements. Especially, with the straight measurement pipe 2, the resonant frequency changes with the variation of the axial force working on the measurement pipe 2, generating erroneous measurements.

As described above, amendments are made according to the technologies disclosed in the publication Tokkouhei-5-69452, Tokkaihei-6-94501, etc., when sensitivity and measured values of the mass flowmeter change with variations in environmental temperature. According to Tokkouhei-5-69452, two temperature sensors are mounted on the supporters 4a and 4b, and the portion indicating a temperature identical to that of the measurement pipe 2. The signals from the two temperature sensors are input to a correction circuit, and the flow signals from the two vibration sensors are also input to the correction circuit to be suitably corrected. According to Tokkaihei-6-94501, the measured flow value is corrected corresponding to the temperature of the measurement pipe 2. To attain this, the system includes a temperature sensor for detecting the temperature of the measurement pipe 2, and a length change sensor (for example, a deformation gauge such as a strain gauge) for correcting a measured value depending on the length and stress of the measurement pipe 2, and each signal is input to a correction circuit. If the temperature is measured on the measurement pipe 2 and the supporters 4a and 4b as in Tokkouhei-5-69452, and a change according to the change in Young's modulus and the axial force on the measurement pipe 2 are estimated indirectly, then there is a temperature gradient along the measurement pipe 2, depending on the difference between the fluid temperature and the environmental temperature, even when the temperatures themselves are stable. If the fluid temperature and environmental temperature are in a transitional state, each shows irregular changes. Therefore, if the temperature measurement point at which an average temperature of the measurement pipe 2 and supporters 4a and 4b can be obtained is not fixed in each of the above described states, measured values may not be corrected appropriately at the specific point where the temperature is measured. If the deformation of the measurement pipe 2 is measured as in the Tokkaihei-6-94501, it is directly measured. Therefore, this ensures accurate deformation correction, however, because it is necessary to fix a strain gauge and the like directly to the measurement pipe 2, the vibration characteristics of the measurement pipe 2 may be badly affected, this produces a problem with the stability of measurement. To avoid this undesired influence, a mass is mounted on each side of the measurement pipe 2, and a strain gauge is applied to the outer side of the mass. At this time, the volume of the mass must be large with respect to the measurement pipe 2, generating another problem that the mass flow meter becomes large and slow.

There is another configuration in which a strain gauge is applied to the supporters 4a and 4b. However, since the rigidity of the supporters 4a and 4b must be large enough to allow stable vibration of the measurement pipe 2, the sectional area of the measurement pipe 2 is much smaller than that of the supporters, and the deformation generated on the supporters 4a and 4b is much smaller than that on the measurement pipe 2. Therefore, there is a problem of a large error in the method of estimating the deformation on the measurement pipe 2, based on the deformation of the supporters 4a and 4b. Although an embodiment off measuring the length of the measurement pipe 2 is disclosed with a length change slot, the structure is too complicated to be considered acceptable.

SUMMARY OF THE INVENTION

The first object of the present invention is to improve the measurement precision of the vibration measuring instrument at a low cost and without a complicated construction.

The second object of the present invention is to reduce (or remove) the influence of density changes of the fluid to be measured on the measurement precision of the vibration measuring instrument, and to accurately correct the change in the measured value resulting from a density change of the fluid to be measured and a change in the axial force on the measurement pipe.

The resonant frequency of a measurement pipe alters with a variation of the axial force (stress) T. The difference with a change in the axial force of constant $\lambda_n$ (T) determined by the boundary condition and vibration mode depends on each vibration mode. Therefore, the resonant frequency ratio of each vibration mode changes with a change in an axial force.

That is, the resonant frequency ratio between each mode changes linearly with a change in the axial force. This is effective for the resonant frequency ratio between optional modes.

It indicates that the axial force working on the measurement pipe can be obtained by measuring the resonant frequency between modes. The present invention enables an accurate measurement to be realized by correcting the change in flow measurement sensitivity with the change in axial force working on the measurement pipe, corresponding to the resonant frequency ratio. Similarly, a measured density value is corrected based on the resonant frequency ratio.

According to other characteristics of the present invention, the influence of a density change on the resonant frequency can be reduced by mounting each adjustment mass to the mounting position of the mass of the vibration generator or vibration sensor, or the vibration sensor on the measurement pipe, and the position symmetrical with the mounting position of the vibration generator or vibration sensor on the measurement pipe.

DESCRIPTION OF THE PREFERRED EMBODIMENTS

Figure 4:
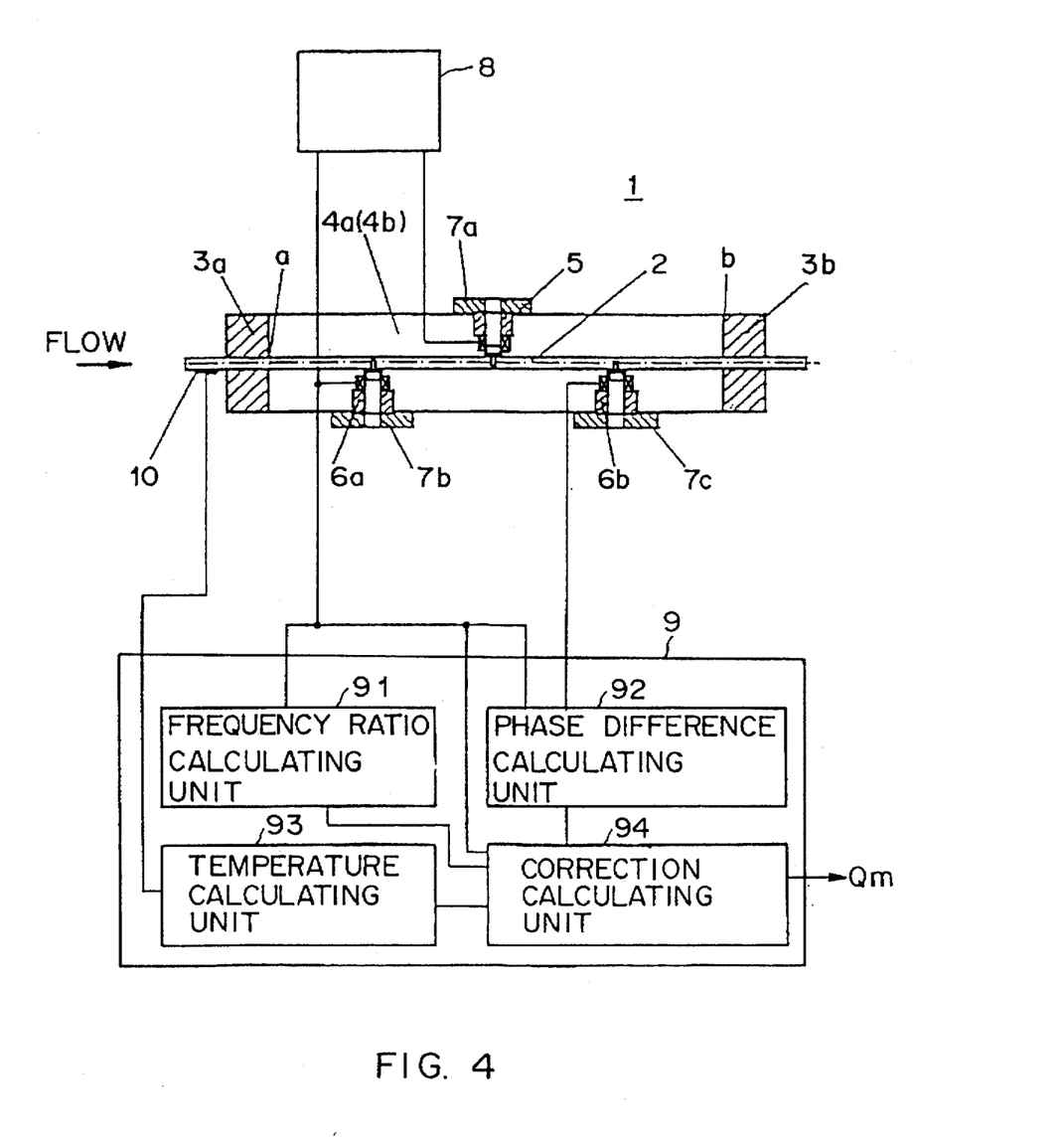
FIG. 4 shows the vibration measuring instrument according to the first embodiment of the present invention.

FIG. 4 shows the configuration according to the first embodiment of the present invention. A detecting unit 1 comprises a straight measurement pipe 2; right and left fixtures 3a and 3b for fixing the vibrating sections a and b of the measurement pipe 2; supporters 4a and 4b (only 4a is shown in FIG. 4) fixed to the fixtures 3a and 3b with screws or by soldering, etc., or designed as being combined with the fixtures 3a and 3b so that the vibrations of the fixtures 3a and 3b cancel each other; and a vibration generator 5, comprising coils fixed to the supporters 4a and 4b with an adapter 7a and a magnet fixed at the central portion of the measurement pipe 2, for vibrating the measurement pipe 2 at its resonant frequency.

The detecting unit 1 further comprises, as the vibration generator 5, speed detecting sensors (or displacement sensors or acceleration sensors) 6a and 6b, comprising magnets fixed symmetrically to the vibration generator 5 on the measurement pipe 2, with the coils fixed to the supporters 4a and 4b with the adapters 7b and 7c, for detecting the vibration of the measurement pipe 2.

As clearly shown in FIG. 4, the characteristics of the first embodiment are a temperature sensor 10 added to the detecting unit 1; and a frequency ratio calculating unit 91, temperature calculating unit 93, and correction calculating unit 94 added to a signal processing circuit 9. Other features are the same as the construction shown in FIG. 1. Therefore, the explanation below concentrates on the differences between the present invention and the prior art.

As shown in the above described equations (5) and (9) or (12) and (13), the phase or time difference of the output signal from the speed sensors 6a and 6b generated in proportion to the mass flow is a function of Young's modulus E and axial force T. Therefore, the output of the temperature sensor 10 is converted into a temperature signal by the temperature calculating unit 93. Then, the output of the speed sensor 6a, that is, the resonant frequency, is input to the frequency ratio calculating unit 91, and the resonant frequency ratio, which depends on the configuration of the detecting unit 1 and the current driving condition, is calculated.

The correction calculating unit 94 receives the outputs from the frequency ratio calculating unit 91, phase difference calculating unit 92, temperature calculating unit 93, and speed sensor 6a. The phase difference signal from the phase difference calculating unit 92 is corrected by the resonant frequency of the measurement pipe obtained by the speed sensor 6a, and is converted into a time difference signal. The correction calculating unit 94 corrects the time difference signal according to the temperature signal from the temperature calculating unit 93, and the sensitivity correction signal which alters with a change in the axial force according to the resonant frequency ratio signal from the frequency ratio calculating unit 91.

That is, with the above described vibration measuring instrument, the ratio of the resonant frequency between the first and second vibration modes is obtained, and the measured value is corrected based on these resonant frequency ratios. First, the resonant frequency ωn of the n-th mode is obtained by the following equation (15).

$$\omega = \lambda n \ (T)^2/L^2 \cdot (EI/\rho))^{1/2} \quad (15)$$

where

λn (T): coefficient determined by the resonant condition of the measurement pipe and the vibration mode T: axial force L: length of measurement pipe 2

E: Young's modulus for measurement pipe

I: secondary sectional moment of measurement pipe

ρ: linear density of measurement pipe containing fluid

According to equation (15), the resonant frequency ratio γnm of the n-th mode to the m-th mode is calculated as follows.

$$\omega m/\omega n = \lambda m \ (T)^2/\lambda n \ (T)^2 = \gamma nm \ (T) \quad (16)$$

Figure 5A:
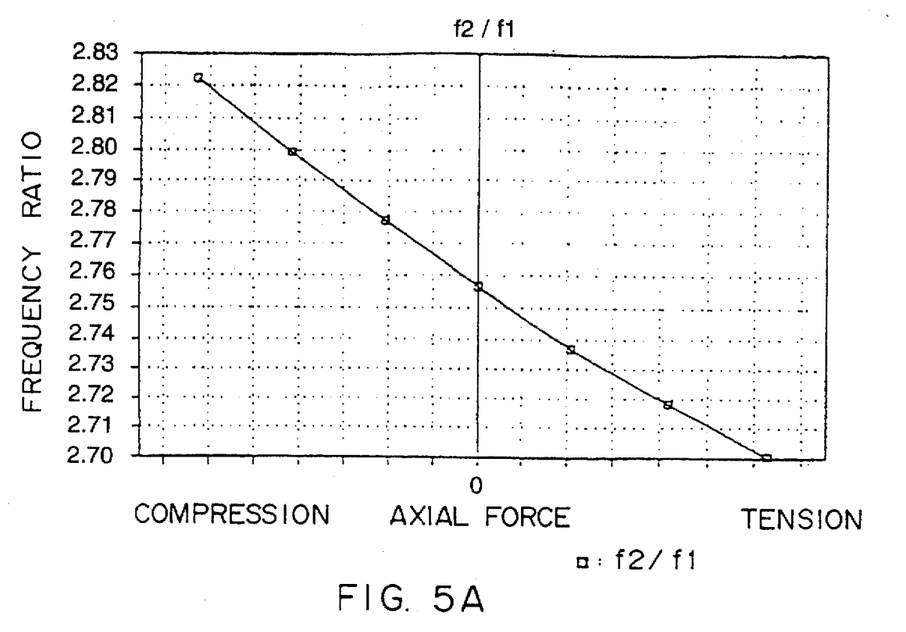
FIG. 5 is a graph showing an example of the relationship between the axial force on a measurement pipe and the resonant frequency ratio.
Figure 5B:
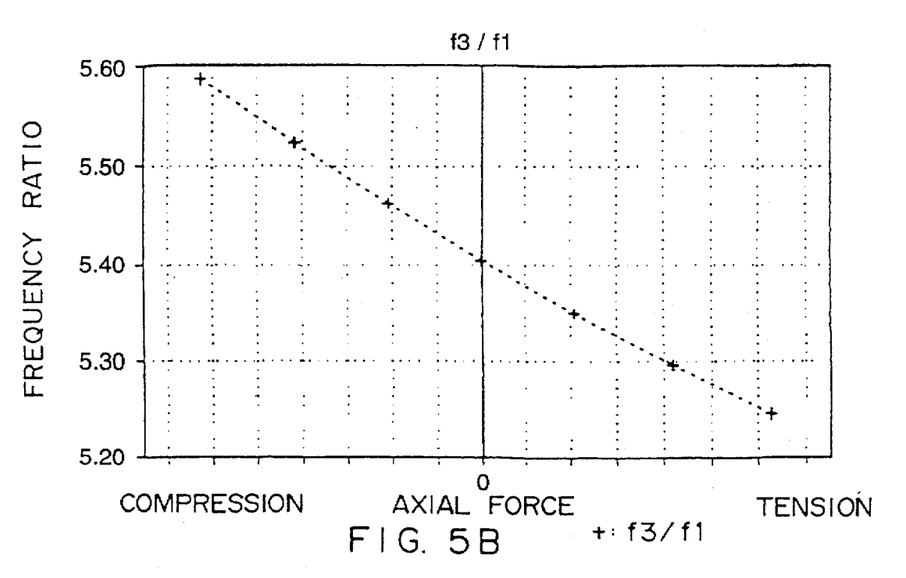

It refers to the function of the axial force T only as shown in FIGS. 5A and 5B. FIG. 5A shows the ratio of the basic mode resonant frequency to the resonant frequency of the second mode, and the relation to the axial force when the axial force working on the measurement pipe 2 shows a change. FIG. 5B shows the ratio of the basic mode resonant frequency to the resonant frequency of the third mode and the relation to the axial force. According to equation (16), for example, the ratio of the basic mode resonant frequency to the resonant frequency of a higher order mode (normally the resonant frequency ratio between two optional modes) is calculated, and the change in the sensitivity with the change in the axial force working on the measurement pipe is corrected in addition to the temperature correction. Therefore, the configuration of the detecting unit is not complicated, the vibration measuring instrument can be operated stably, and precise measurement can be made even with a transitional change in temperature.

According to the above described first embodiment, the output from the speed sensor 6a is input for the correction calculating unit 94. However, the output from the speed sensor 6b can also be input to the correction calculating unit 94. Similarly, a measured density value of the density meter can be corrected depending on the temperature and resonant frequency ratio.

The measurement pipe has been described as having a uniform section. Actually, according to the first embodiment, a measurement pipe 2 is directly provided with a vibration generator 5 for vibrating the measurement pipe 2, which is an added mass to the measurement pipe, and first and second speed detecting sensors 6a and 6b for detecting the vibration of the measurement pipe 2. If the measurement pipe has a uniform section, the frequency ratio between optional two modes indicates a function of only an axial force T. If the measurement pipe has the above described added mass, it should be taken into account that the frequency ratio alters with the variation of the density of the measured fluid flowing through the measurement pipe.

Figure 6:
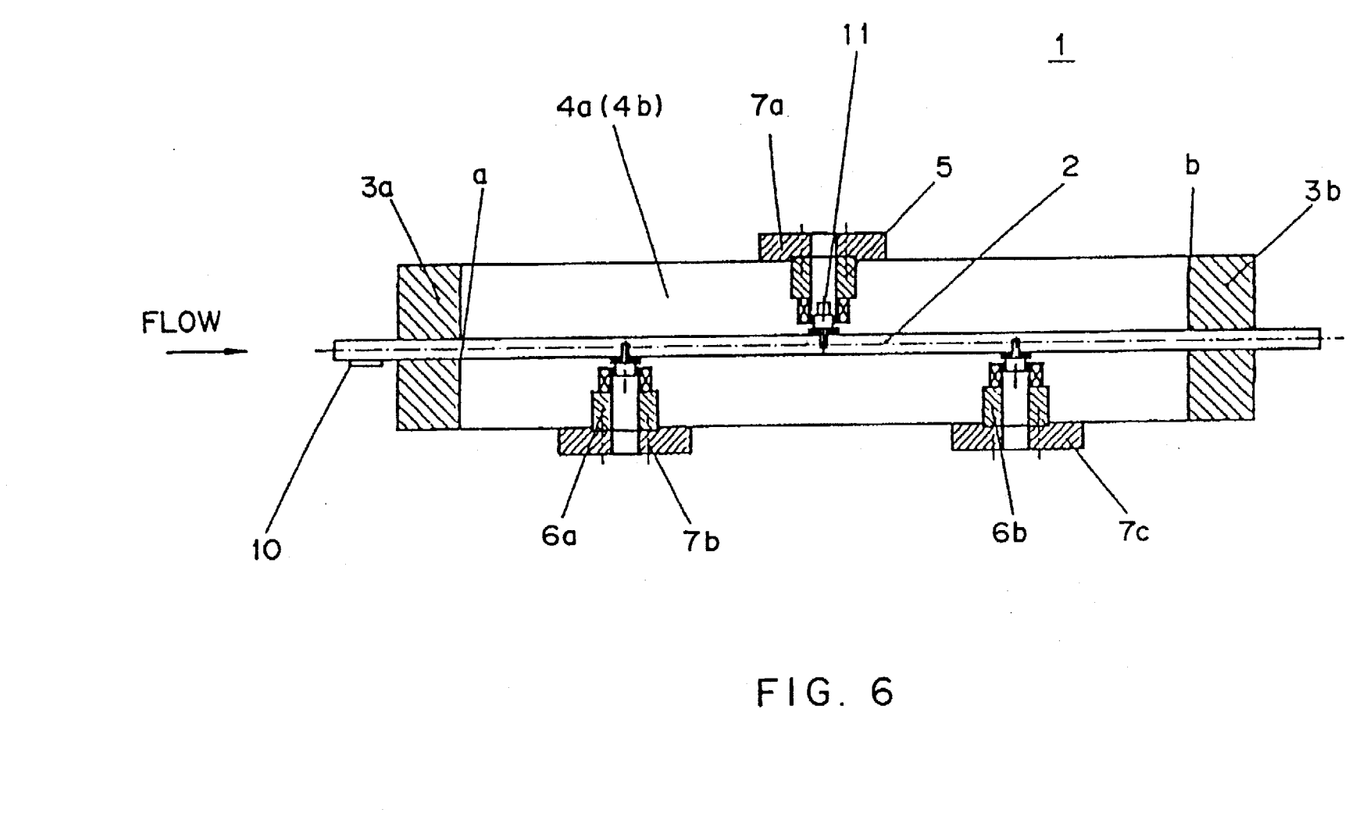
FIG. 6 shows the configuration of the vibration measuring instrument according to the second embodiment of the present invention.

FIG. 6 shows the configuration showing the second embodiment of the present invention, taking into account the problem of the density-dependent frequency ratio.

The detecting unit 1 is equipped with the magnet of the vibration generator 5 and an adjustment mass 11 for use in adjusting the mass of the fixture so that the resonant frequency ratio between the first and second vibration modes of the straight measurement pipe 2 can be independent of the influence of a change in the fluid density in the measurement pipe 2. Other features are the same as those of the configuration shown in FIG. 4 and accordingly the detailed explanation is omitted here.

Described below are the considerations for the above listed configuration.

The density dependency δ13, [%/(Kg/Liter)] of the resonant frequency ratio of the basic mode resonant frequency to the third mode resonant frequency, with the measured fluid density changed from 1 [Kg/Liter] to b [Kg/Liter] can be defined as follows.

$$\delta 13 = 100 \ [\gamma 13, b - \gamma 13, 1]/[\gamma 13, 1 \ (b-1)] \quad (17)$$

where

γ13,b: resonant frequency ratio of the basic mode to the third mode when the measured fluid density is b [Kg/Liter].

γ13,1: resonant frequency ratio of the basic mode to the third mode when the measured fluid density is 1 [Kg/Liter].

Figure 7:
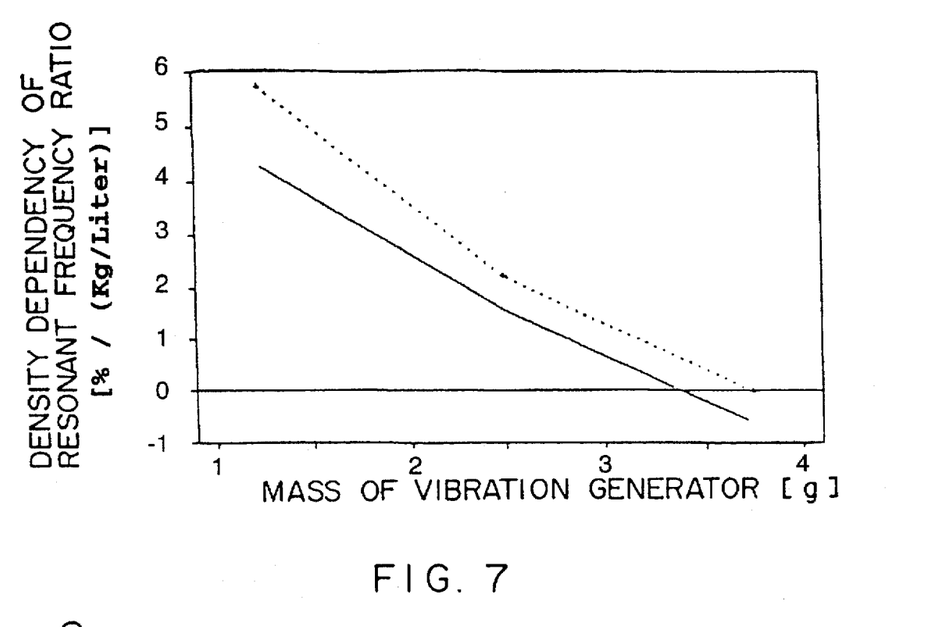
FIG. 7 shows the characteristics of the relationship between the mass of the vibration generator and the density-dependency of the resonant frequency ratio.

FIG. 7 shows an example of the relationship between the calculated value using the above listed equation (17) and the actual value (solid lines indicate the calculated value and broken lines indicate the actual value) of the density dependency of the resonant frequency ratio with the mass (g) of the vibration generator 5 changed. It indicates that the density dependency of the resonant frequency ratio alters with the function of the mass of the vibration generator 5, that is the mass of the vibration generator 5. Therefore, as with the above described embodiment, adjusting the mass of the vibration generator 5 reduces or finally removes the influence of a change in density on the resonant frequency ratio.

Figure 8:
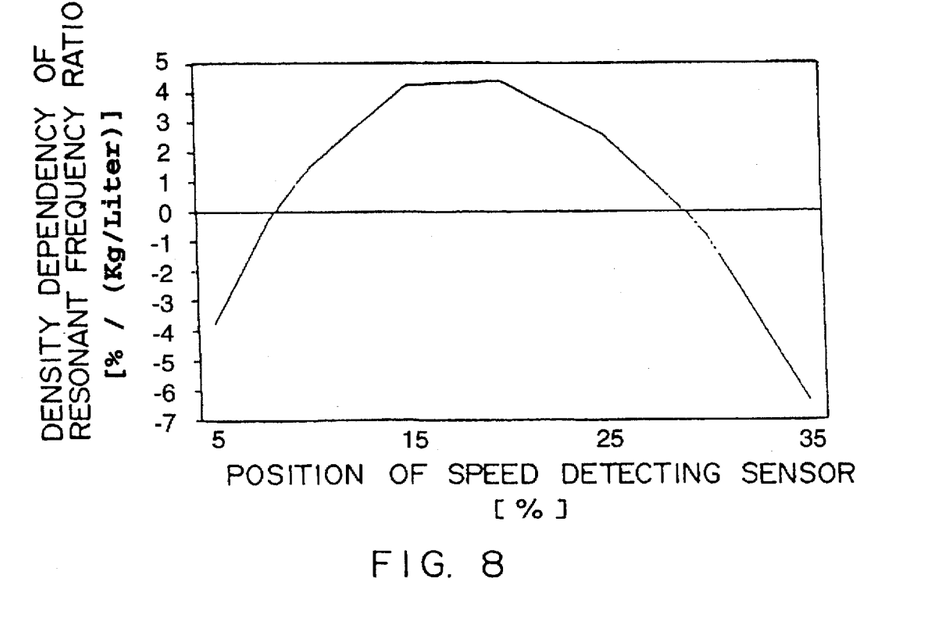
FIG. 8 shows the characteristics of the relationship between the position of the vibration detection sensor and the density-dependency of the resonant frequency ratio.

FIG. 8 shows the calculation result of the density dependency of the ratio of the basic mode resonant frequency and the third mode resonant frequency to the position of the speed sensors 6a and 6b with the fluid density in a sample measurement pipe 2 changed. In FIG. 8, the positions of the speed sensors 6a and 6b are represented by the distance between the fixtures 3a and 3b as a percentage of the length of the measurement pipe 2.

That is, as clearly shown in FIG. 2, the density dependency of the resonant frequency ratio also changes with the mounting positions of the speed sensors 6a and 6b. Therefore, adjusting the positions of the speed sensors 6a and 6b reduces or finally removes the influence of a change in the fluid density in the measurement pipe 2 on the resonant frequency ratio.

Figure 9:
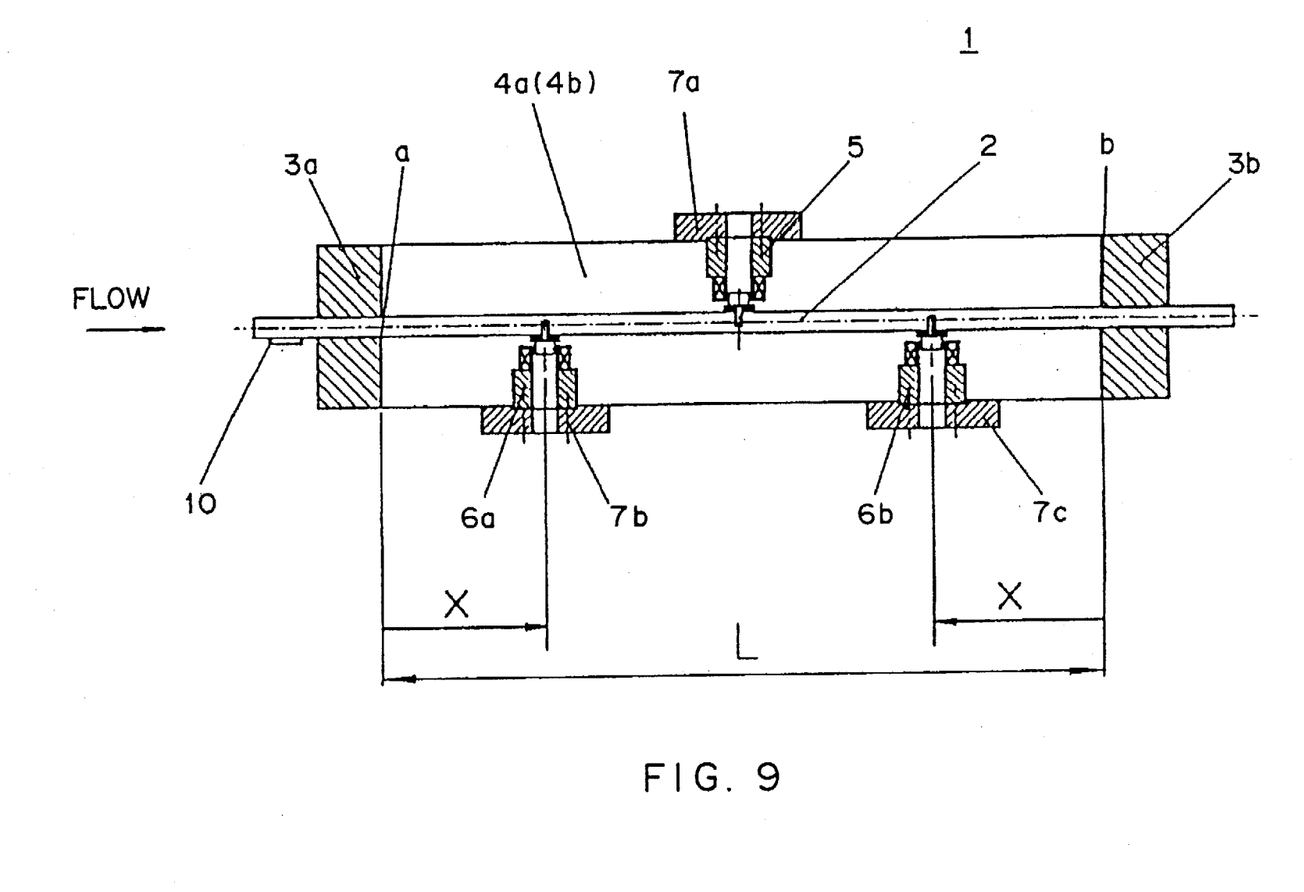
FIG. 9 shows the configuration of the vibration measuring instrument according to the third embodiment of the present invention.

FIG. 9 shows the configuration according to the third embodiment of the present invention.

That is, with the third embodiment, the speed sensors 6a and 6b are mounted symmetrically about the vibration generator 5 on the measurement pipe 2 at the positions x from the fixtures 3a and 3b respectively. The distance x refers to a value at which the resonant frequency ratios of the first and second vibration modes of the measurement pipe 2 are not influenced by a change in the density of the fluid in the measurement pipe 2.

Performing the above described processes allows the mass of the speed sensors 6a and 6b to be adjusted instead of adjusting the mass of the vibration generator 5 mounted to the measurement pipe 2, as shown in FIG. 6.

Figure 10:
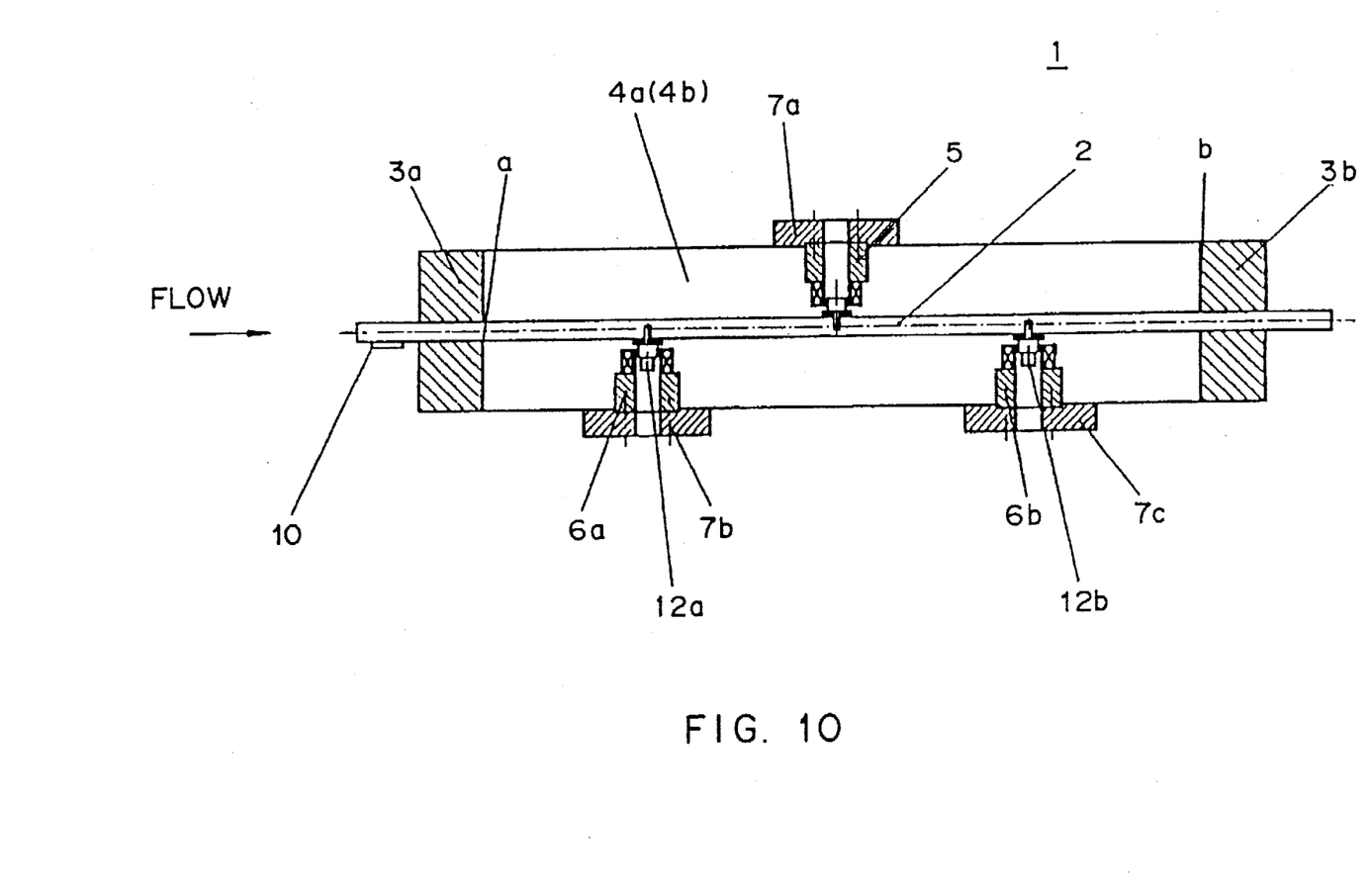
FIG. 10 shows the configuration of the vibration measuring instrument according to the fourth embodiment of the present invention.

FIG. 10 shows the fourth embodiment in which adjustment masses 12a and 12b are provided to adjust the masses of the magnets of the speed sensors 6a and 6b and the masses of the fixtures. This configuration can also reduce the influence of a change in the density of the fluid in the measurement pipe 2 on the resonant frequency ratios of the optional two vibration modes.

Figure 11:
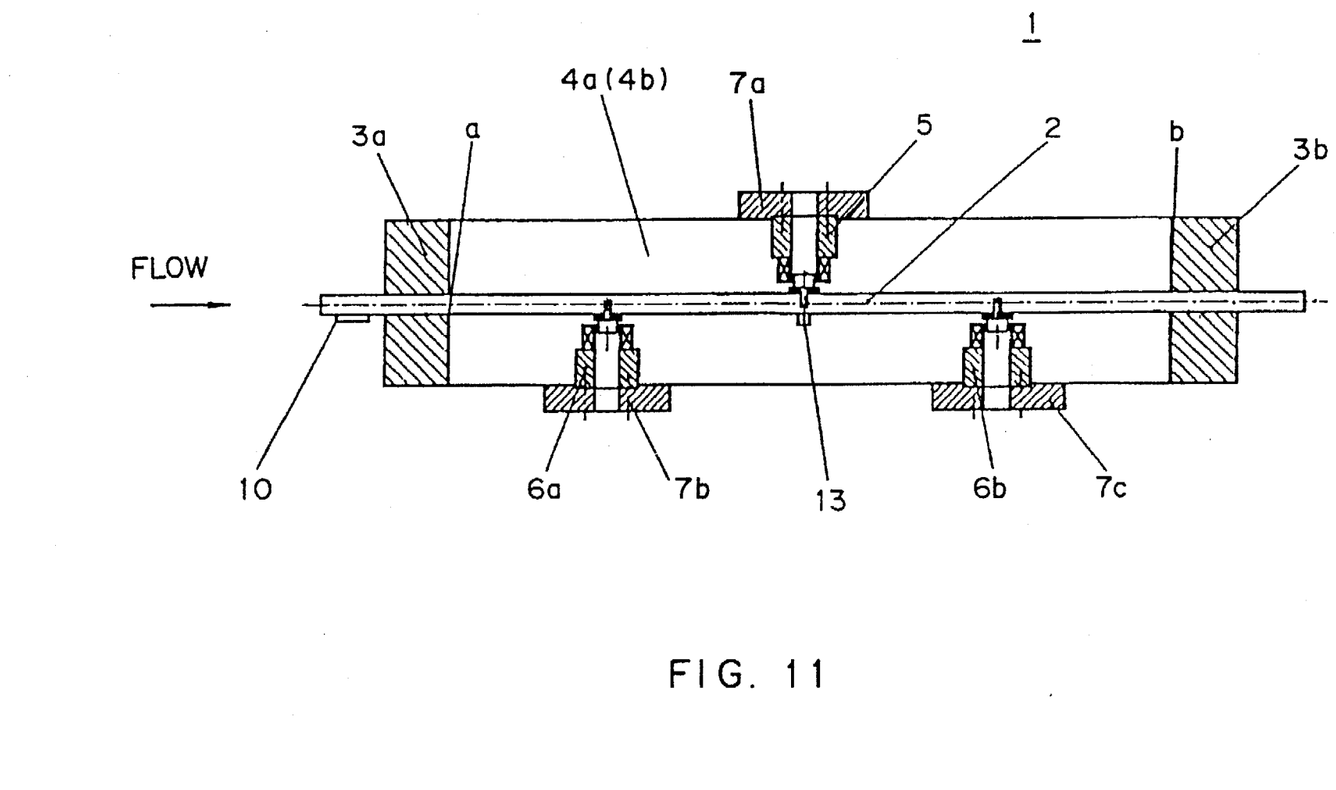
FIG. 11 shows the configuration of the vibration measuring instrument according to the fifth embodiment of the present invention.
Figure 12:
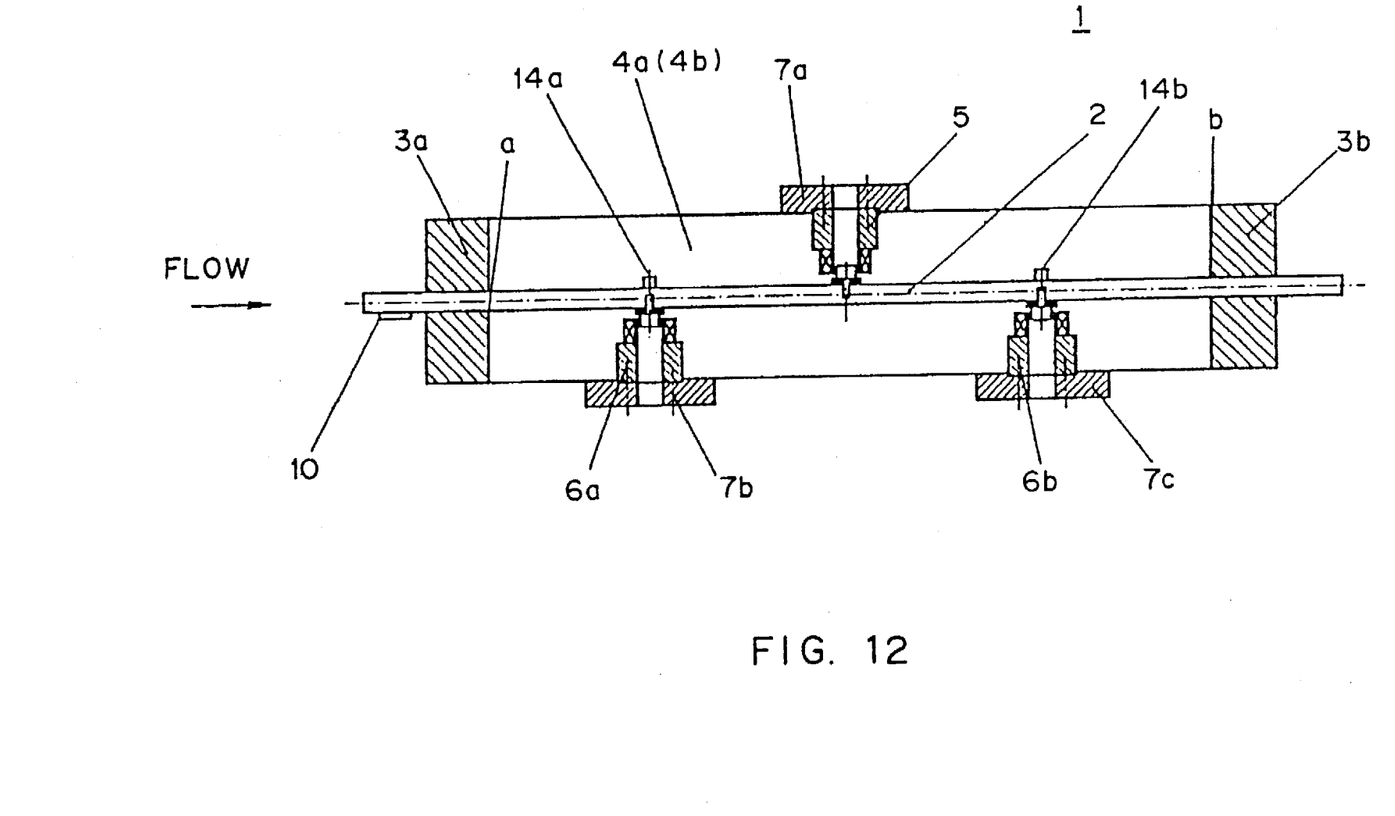
FIG. 12 shows the configuration of the vibration measuring instrument according to the sixth embodiment of the present invention.

The need for adjusting the masses of the vibration generator 5 and speed sensors 6a and 6b can be replaced using the configuration shown in FIGS. 11 and 12.

That is, the fifth embodiment shown in FIG. 11 comprises an adjustment mass 13 provided at a predetermined position on the measurement pipe 2, to enable the adjustment mass 13 to counter-balance the vibration generator 5. The sixth embodiment shown in FIG. 12 comprises adjustment masses 14a and 14b provided at predetermined positions on the measurement pipe 2, to enable the adjustment masses 14a and 14b to counter-balance the speed sensors 6a and 6b.

Thus, adjusting the masses of the vibration generator 5 and speed sensors 6a and 6b, or adjusting the mounting positions of the vibration generator 5, speed sensors 6a and 6b, and additional masses 13, 14a, and 14b on the measurement pipe, reduces the influence of a change in the density of the fluid in the measurement pipe 2 on the resonant frequency of the optional two vibration modes.

That is, according to the second through fourth embodiments, adjusting the masses of the vibration generator 5 on the measurement pipe 2, and the speed sensors 6a and 6b or the positions of the speed sensors 6a and 6b on the measurement pipe 2, easily reduces the influence of a change in the density of the fluid in the measurement pipe 2 on the resonant frequency ratio of the first and second vibration modes. According to the fifth and sixth embodiments, mounting the adjustment masses 13, 14a, and 14b to counter-balance the vibration generator 5 and speed sensors 6a and 6b, reduces the influence of the position of the detecting unit 1.

What is claimed is:

1. A vibration measuring instrument capable of measuring at least one of a mass flow and density of a fluid flowing through at least one vibrated straight measurement pipe, comprising:

supporting means for supporting the measurement pipe;
   vibration generator means for vibrating the measurement pipe;
   first and second vibration detecting means, mounted at positions symmetrically about an axial center of the measurement pipe, for detecting vibration of the measurement pipe;
   temperature detecting means for detecting the temperature of the measurement pipe;
   frequency ratio calculating means for calculating a ratio of a resonant frequency of a first vibration mode to the resonant frequency of a second vibration mode of the measurement pipe, according to at least one output from said first and second vibration detecting means; and
   correcting means for correcting a measured value according to the ratio between the resonant frequencies; wherein
   a mass of said vibration generator means is set such that a change in resonant frequency ratio approaches zero when density of a fluid through the measurement pipe changes.

2. The vibration measuring instrument according to claim 1, wherein said first vibration mode is a basic mode of a measurement pipe vibration; and
   said second vibration mode is a secondary mode of a measurement pipe vibration.

3. The vibration measuring instrument according to claim 1, wherein said first vibration mode is a basic mode of a measurement pipe vibration; and
   said second vibration mode is a third mode of a measurement pipe vibration.

4. A vibration measuring instrument comprising:

a straight measurement pipe;
   supporting means for supporting said measurement pipe;
   vibration generator means for vibrating said measurement pipe;
   first and second vibration detecting means, provided symmetrically about an axial center of said measurement pipe, for detecting vibration of said measurement pipe;
   temperature detecting means for measuring a temperature of said measurement pipe;
   frequency ratio calculating means for calculating a ratio of a resonant frequency of a first vibration mode to the resonant frequency of a second vibration mode of the measurement pipe, according to at least one output from said first and second vibration detecting means;
   phase difference calculating means for obtaining a phase difference in a vibration generated on said measurement pipe, based on outputs of said first and second vibration detecting means; and
   correcting means for correcting the phase difference, based on a temperature measured by said temperature detecting means and a resonant frequency ratio obtained by said frequency ratio calculating means; wherein
   a mass of said vibration generator means is set such that a change in resonant frequency ratio approaches zero when density of a fluid through the measurement pipe changes.

5. A vibration measuring method of measuring at least one of a mass flow and density of a fluid flowing through at least one vibrated straight measurement pipe, comprising the steps of:

calculating resonant frequencies of a plurality of vibration modes of the measurement pipe;
   reducing an influence of a change in the density of the fluid in the straight measurement pipe on the resonant frequency ratio of two vibration modes; and
   correcting a measured value of at least one of a mass flow and density on condition that a change in a resonant frequency with a change in an axial force on the measurement pipe depends on each vibration mode.

6. A vibration measuring instrument capable of measuring at least one of a mass flow and density of a fluid flowing through at least one vibrated straight measurement pipe, comprising:

supporting means for supporting the measurement pipe;
   vibration generator means for vibrating the measurement pipe;
   first and second vibration detecting means, mounted at positions symmetrically about an axial center of the measurement pipe, for detecting vibration of the measurement pipe;
   temperature detecting means for detecting the temperature of the measurement pipe;

frequency ratio calculating means for calculating a ratio of a resonant frequency of a first vibration mode to the resonant frequency of a second vibration mode of the measurement pipe, according to at least one output from said first and second vibration detecting means; and correcting means for correcting a measured value according to the ratio between the resonant frequencies; wherein mounting positions of said first and second vibration detecting means on the measurement pipe are set such that a change in resonant frequency ratio approaches zero when density of a fluid through the measurement pipe changes.

7. A vibration measuring instrument capable of measuring at least one of a mass flow and density of a fluid flowing through at least one vibrated straight measurement pipe, comprising:

supporting means for supporting the measurement pipe;

vibration generator means for vibrating the measurement pipe;

first and second vibration detecting means, mounted at positions symmetrically about an axial center of the measurement pipe, for detecting vibration of the measurement pipe;

temperature detecting means for detecting the temperature of the measurement pipe;

frequency ratio calculating means for calculating a ratio of a resonant frequency of a first vibration mode to the resonant frequency of a second vibration mode of the measurement pipe, according to at least one output from said first and second vibration detecting means; and correcting means for correcting a measured value according to the ratio between the resonant frequencies; wherein masses of said first and second vibration detecting means on the measurement pipe are set such that a change in resonant frequency ratio approaches zero when density of a fluid through the measurement pipe changes.

8. A vibration measuring instrument capable of measuring at least one of a mass flow and density of a fluid flowing through at least one vibrated straight measurement pipe, comprising:

supporting means for supporting the measurement pipe;

vibration generator means for vibrating the measurement pipe;

first and second vibration detecting means, mounted at positions symmetrically about an axial center of the measurement pipe, for detecting vibration of the measurement pipe;

temperature detecting means for detecting the temperature of the measurement pipe;

frequency ratio calculating means for calculating a ratio of a resonant frequency of a first vibration mode to the resonant frequency of a second vibration mode of the measurement pipe, according to at least one output from said first and second vibration detecting means;

correcting means for correcting a measured value according to the ratio between the resonant frequencies; and an adjustment mass provided in symmetry with mounting position of said vibration generator means, such that a change in resonant frequency ratio approaches zero when density of a fluid through the measurement pipe changes.

9. A vibration measuring instrument capable of measuring at least one of a mass flow and density of a fluid flowing through at least one vibrated straight measurement pipe, comprising:

supporting means for supporting the measurement pipe;

vibration generator means for vibrating the measurement pipe;

first and second vibration detecting means, mounted at positions symmetrically about an axial center of the measurement pipe, for detecting vibration of the measurement pipe;

temperature detecting means for detecting the temperature of the measurement pipe;

frequency ratio calculating means for calculating a ratio of a resonant frequency of a first vibration mode to the resonant frequency of a second vibration mode of the measurement pipe, according to at least one output from said first and second vibration detecting means;

correcting means for correcting a measured value according to the ratio between the resonant frequencies; and adjustment masses provided in symmetry with mounting positions of said first and second vibration detecting means, such that a change in resonant frequency ratio approaches zero when density of a fluid through the measurement pipe changes.

10. A vibration measuring instrument comprising:

a straight measurement pipe;

supporting means for supporting said measurement pipe;

vibration generator means for vibrating said measurement pipe;

first and second vibration detecting means, provided symmetrically about an axial center of said measurement pipe, for detecting vibration of said measurement pipe;

temperature detecting means for measuring a temperature of said measurement pipe;

frequency ratio calculating means for calculating a ratio of a resonant frequency of a first vibration mode to the resonant frequency of a second vibration mode of the measurement pipe, according to at least one output from said first and second vibration detecting means;

phase difference calculating means for obtaining a phase difference in a vibration generated on said measurement pipe, based on outputs of said first and second vibration detecting means; and correcting means for correcting the phase difference, based on a temperature measured by said temperature detecting means and a resonant frequency ratio obtained by said frequency ratio calculating means; wherein mounting positions of said first and second vibration detecting means on the measurement pipe are set such that a change in resonant frequency ratio approaches zero when density of a fluid through the measurement pipe changes.

11. A vibration measuring instrument comprising:

a straight measurement pipe;

supporting means for supporting said measurement pipe;

vibration generator means for vibrating said measurement pipe;

first and second vibration detecting means, provided symmetrically about an axial center of said measurement pipe, for detecting vibration of said measurement pipe;

temperature detecting means for measuring a temperature of said measurement pipe;

frequency ratio calculating means for calculating a ratio of a resonant frequency of a first vibration mode to the resonant frequency of a second vibration mode of the measurement pipe, according to at least one output from said first and second vibration detecting means;

phase difference calculating means for obtaining a phase difference in a vibration generated on said measurement pipe, based on outputs of said first and second vibration detecting means; and correcting means for correcting the phase difference, based on a temperature measured by said temperature detecting means and a resonant frequency ratio obtained by said frequency ratio calculating means; wherein masses of said first and second vibration detecting means on the measurement pipe are set such that a change in resonant frequency ratio approaches zero when density of a fluid through the measurement pipe changes.

12. A vibration measuring instrument comprising:

straight measurement pipe;

supporting means for supporting said measurement pipe;

vibration generator means for vibrating said measurement pipe;

first and second vibration detecting means, provided symmetrically about an axial center of said measurement pipe, for detecting vibration of said measurement pipe;

temperature detecting means for measuring a temperature of said measurement pipe;

frequency ratio calculating means for calculating a ratio of a resonant frequency of a first vibration mode to the resonant frequency of a second vibration mode of the measurement pipe, according to at least one output from said first and second vibration detecting means;

phase difference calculating means for obtaining a phase difference in a vibration generated on said measurement pipe, based on outputs of said first and second vibration detecting means; and correcting means for correcting the phase difference, based on a temperature measured by said temperature detecting means and a resonant frequency ratio obtained by said frequency ratio calculating means; and an adjustment mass provided in symmetry with mounting position of said vibration generator means, such that a change in resonant frequency ratio approaches zero when density of a fluid through the measurement pipe changes.

13. A vibration measuring instrument comprising:

a straight measurement pipe;

supporting means for supporting said measurement pipe;

vibration generator means for vibrating said measurement pipe;

first and second vibration detecting means, provided symmetrically about an axial center of said measurement pipe, for detecting vibration of said measurement pipe;

temperature detecting means for measuring a temperature of said measurement pipe;

frequency ratio calculating means for calculating a ratio of a resonant frequency of a first vibration mode to the resonant frequency of a second vibration mode of the measurement pipe, according to at least one output from said first and second vibration detecting means;

phase difference calculating means for obtaining a phase difference in a vibration generated on said measurement pipe, based on outputs of said first and second vibration detecting means; and correcting means for correcting the phase difference, based on a temperature measured by said temperature detecting means and a resonant frequency ratio obtained by said frequency ratio calculating means; and adjustment masses provided in symmetry with mounting positions of said first and second vibration detecting means, such that a change in resonant frequency ratio approaches zero when density of a fluid through the measurement pipe changes.

* * * * *